United States Patent
Shimabayashi et al.

(10) Patent No.: US 7,674,898 B2
(45) Date of Patent: Mar. 9, 2010

(54) ANHYDROUS CRYSTAL OF β-LACTAM COMPOUND AND METHOD FOR PREPARATION THEREOF

(75) Inventors: Akihiro Shimabayashi, Tokushima (JP); Shigetoshi Yaguchi, Tokushima (JP)

(73) Assignees: Otsuka Chemical Co., Ltd., Osaka (JP); Taiho Pharmaceutical Co., Ltd., Tokyo (JP)

( * ) Notice: Subject to any disclaimer, the term of this patent is extended or adjusted under 35 U.S.C. 154(b) by 1646 days.

(21) Appl. No.: 10/476,221

(22) PCT Filed: Jul. 23, 2001

(86) PCT No.: PCT/JP01/06321
§ 371 (c)(1), (2), (4) Date: Apr. 5, 2004

(87) PCT Pub. No.: WO02/090363
PCT Pub. Date: Nov. 14, 2002

(65) Prior Publication Data
US 2004/0162277 A1 Aug. 19, 2004

(30) Foreign Application Priority Data
May 1, 2001 (JP) ............................. 2001-134187

(51) Int. Cl.
*C07D 499/87* (2006.01)
(52) U.S. Cl. ................................... 540/310
(58) Field of Classification Search .............. 540/310
See application file for complete search history.

(56) References Cited

U.S. PATENT DOCUMENTS 4,562,073 A * 12/1985 Micetich et al. ............ 424/114
4,626,384 A * 12/1986 Tanaka et al. .............. 540/306
4,925,934 A   5/1990 Taniguchi et al.

OTHER PUBLICATIONS

Translation of KR20000061217 (Oct. 16, 2000).*
Lin et al., Huaxue Gongye Yu Gongcheng (Tianjin, China) (2002), 19(3), 219-224, 273.*
Deng et al., Zhongguo Yaowu Huaxue Zazhi (2001), 11(2), 93-95.*
Translation of Deng et al., Zhongguo Yaowu Huaxue Zazhi (2001), 11(2), 93-95.*
Xiangguo, Shanghai Dier Yike Daxue Xuebao (2000), 20(5), 388-391.*
Translation of Xiangguo, Shanghai Dier Yike Daxue Xuebao (2000), 20(5), 388-391.*
Bai, Fine Chemicals -Dalian- 2001, vol. 18; Part 11, pp. 634-637.*
Translation of Bai, Fine Chemicals -Dalian- 2001, vol. 18; Part 11, pp. 634-637.*
Partial translation of Lin et al., Huaxue Gongye Yu Gongcheng (Tianjin, China) (2002), 19(3), 219-224, 273.*

* cited by examiner

*Primary Examiner*—Mark L Berch
(74) *Attorney, Agent, or Firm*—Wenderoth, Lind & Ponack, L.L.P.

(57) ABSTRACT

The present invention provides anhydrous crystals of β-lactam compound represented by the formula:

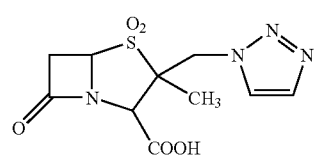

(1)

The β-lactam compound of the invention is produced by heating an aqueous solution of a salt of the β-lactam compound and adjusting the pH of the aqueous solution to 3 or lower. The β-lactam compound has excellent storage stability.

1 Claim, No Drawings

US 7,674,898 B2

ANHYDROUS CRYSTAL OF β-LACTAM COMPOUND AND METHOD FOR PREPARATION THEREOF

This application is the U.S. National Phase under 35 U.S.C. §371 of International Application PCT/JP01/06321, filed Jul. 23, 2001, which claims priority of Japanese Patent Application No. 2001-134187, filed May 1, 2001. The International Application was published under PCT Article 21(2) in a language other than English.

TECHNICAL FIELD

The present invention relates to anhydrous crystals of β-lactam compound and a method for preparing the crystals.

BACKGROUND OF THE INVENTION

2-Methyl-2-triazolylmethylpenam-3-carboxylic acid S,S-dioxide, is a β-lactam compound represented by the following formula (1) and generally called "tazobactam":

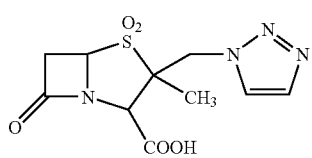

(1)

As tazobactam per se exhibits very weak antibacterial activity, it is not used alone as an antibacterial agent. However, it irreversibly binds to various β-lactamases produced by microorganisms and exhibits ability to inhibit β-lactamase activities. Therefore, tazobactam is used in combination with various existing antibacterial agents that are inactivated by β-lactamases, allowing such antibacterial agents to exhibit their inherent antibacterial activity against β-lactamase-producing microorganisms (Katsuji SAKAI, *Recent Antibiotics Manual* 10th ed., page 113). For example, pharmaceuticals containing a sodium salt of tazobactam and piperacillin (a type of antibacterial agent inactivated by β-lactamase) as active ingredients are commercially available and widely used.

Heretofore, tazobactam has been produced, according to the method disclosed in Japanese Patent No. 2648750, by reacting cresol and a β-lactam compound represented by formula (2):

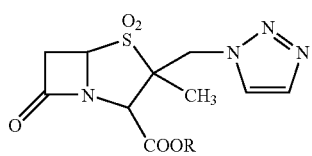

(2)

wherein R represents benzyl having electron-donating substituent(s) on the phenyl ring, diphenylmethyl that may have electron-donating substituent(s) on the phenyl ring(s), or tert-butyl.

Although tazobactam is barely water-soluble, when it is converted into a salt, it becomes water-soluble. Tazobactam is isolated and purified by taking advantage of this property.

In particular, in the aforementioned patent, a reaction mixture containing tazobactam formed is mixed with a basic compound, water and a hydrophobic organic solvent, thereby converting the tazobactam into a salt. Subsequently, the tazobactam salt is extracted into the aqueous layer, and this aqueous layer is acidified to crystallize the desired tazobactam. The above-described patent does not specify the temperature at which the aqueous layer is acidified. In the examples therein, however, the aqueous layer is cooled to 0 to 5° C. and then adjusted to an acidic range.

The tazobactam crystals obtained according to the method disclosed in the aforementioned patent exhibit poor stability and pose a problem of impaired purity due to decomposition after long-term storage at room temperature.

When tazobactam purity decreased even to a small degree, it fails to meet pharmaceutical standards and cannot be formulated. Moreover, due to the decomposition of tazobactam, β-lactamase inhibiting activity is impaired and antibacterial agents used in combination therewith may not sufficiently exhibit their antibacterial activities. Therefore, in order to use a combination of tazobactam and antibacterial agents as a medicament, it is necessary to prevent the purity of tazobactam from being decreased.

To this end, techniques to avoid decrease in purity such as storage under refrigerated conditions are applied to the tazobactam produced according to the aforementioned method.

DISCLOSURE OF THE INVENTION

An object of the present invention is to provide tazobactam crystals having excellent storage stability.

Another object of the present invention is to provide a method for producing tazobactam crystals having excellent storage stability.

The inventors conducted extensive research to achieve the above objectives. As a result, by subjecting tazobactam crystals obtained according to a known method to a specific treatment, the inventors succeeded in obtaining anhydrous crystals that are different from known tazobactam crystals. Furthermore, the inventors found that the anhydrous tazobactam crystals obtained according to such a method has excellent storage stability and can meet the objectives of the present invention. The present invention has been accomplished based on such findings.

The present invention provides anhydrous crystals of the β-lactam compound represented by formula (1):

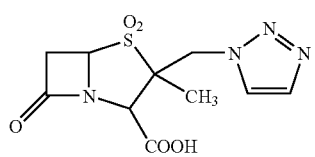

(1)

The present invention provides a method for producing anhydrous crystals of the β-lactam compound, the method comprising heating an aqueous solution of a salt of the β-lactam compound represented by formula (1) above, and adjusting the pH of the aqueous solution to 3 or lower.

The anhydrous crystals of the β-lactam compound represented by formula (1) of the invention consists of 2-methyl-2-triazolylmethylpenam-3-carboxylic acid S,S-dioxide having no water of crystallization. Examples of anhydrous crystals of such β-lactam compound include those having peaks at the following interplanar spacings in the X-ray diffraction spectrum obtained by copper radiation of λ=1.5418 Å through a monochromator, and the like:

| d (interplanar spacings) |
| --- |
| 8.413-9.298 |
| 8.248-9.116 |
| 7.167-7.922 |
| 6.357-7.026 |
| 5.728-6.331 |
| 5.614-6.205 |
| 5.311-5.870 |
| 4.871-5.384 |
| 4.662-5.153 |
| 4.518-4.994 |
| 4.420-4.885 |
| 4.124-4.558 |
| 3.971-4.389 |
| 3.331-3.682 |
| 3.306-3.653 |
| 3.119-3.447 |
| 2.743-3.032 |
| 2.593-2.866 |

Among the anhydrous crystals of the invention that have the X-ray diffraction spectrum peaks (interplanar spacings) decribed above, those having the following interplanar spacings and relative intensities are preferable:

| d (interplanar spacings) | Relative intensities ($I/I_0$) |
| --- | --- |
| 8.413-9.298 | 0.11-0.31 |
| 8.248-9.116 | 0.01-0.40 |
| 7.167-7.922 | 0.29-0.43 |
| 6.357-7.026 | 0.58-0.76 |
| 5.728-6.331 | 0.01-1.00 |
| 5.614-6.205 | 0.38-0.98 |
| 5.311-5.870 | 0.43-0.65 |
| 4.871-5.384 | 0.29-0.57 |
| 4.662-5.153 | 0.80-1.00 |
| 4.518-4.994 | 0.02-0.40 |
| 4.420-4.885 | 0.14-0.22 |
| 4.124-4.558 | 0.01-0.55 |
| 3.971-4.389 | 0.58-0.82 |
| 3.331-3.682 | 0.10-0.50 |
| 3.306-3.653 | 0.09-0.37 |
| 3.119-3.447 | 0.01-0.56 |
| 2.743-3.032 | 0.31-0.57 |
| 2.593-2.866 | 0.01-0.75 |

In the present invention, X-ray diffraction spectra were measured with a RINT 2000/PC (trade name) produced by Rigaku International Corporation.

A method for producing the anhydrous crystalline β-lactam compound represented by formula (1) will be described below.

The anhydrous crystals of the β-lactam compound of the invention is produced, for example, by heating an aqueous solution of a salt of the β-lactam compound represented by formula (1):

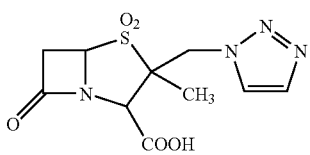

(1)

and adjusting the pH of the aqueous solution to 3 or lower.

The salt of the β-lactam compound represented by formula (1) used as the starting material can be readily prepared by treating tazobactam obtained according to the method disclosed in Japanese Patent No. 2648750 with a basic compound.

The concentration of tazobactam salt in the aqueous solution is not limited, and can be suitably selected from a wide range. In view of crystallization efficiency of the desired anhydrous crystals, workability, etc., the concentration is usually 1 to 50 wt. %, preferably 5 to 20 wt. %.

An aqueous solution of a tazobactam salt can be produced, for example, according to the method disclosed in Japanese Patent No. 2648750. Alternatively, an aqueous solution of the tazobactam salt can be prepared by adding crude tazobactam and a basic compound to water, thereby dissolving tazobactam in water in the form of a salt.

As the basic compounds, known compounds can be widely used, and examples include sodium hydrogen carbonate, potassium hydrogen carbonate, and like alkali metal hydrogen carbonates; sodium carbonate, potassium carbonate, and like alkali metal carbonates; calcium carbonate and like alkaline earth metal carbonates, etc. Among these compounds, preferable are sodium hydrogen carbonate and like alkali metal hydrogen carbonates. These basic compounds can be used alone or in a combination of two or more species.

Examples of tazobactam salts used as the starting material include a sodium salt, a potassium salt, and like alkali metal salts of tazobactam; and a calcium salt and like alkaline earth metal salts of tazobactam.

In the production method of the invention, prior to adjusting the pH of an aqueous solution of a tazobactam salt to 3 or lower, it is necessary to heat the solution of a tazobactam salt. The term "heat(ing)" as used herein is intended to mean elevating the temperature of the aqueous solution of a tazobactam salt to a temperature higher than that of the aqueous solution before the heat treatment. The temperature is not limited insofar as the temperature of the solution is higher than ambient temperature. In the present invention, in view of crystallization efficiency of the desired anhydrous crystals, workability, and economy, the aqueous solution is usually heated to about 20 to about 60° C., preferably about 25 to about 48° C., and more preferably about 30 to about 40° C.

The pH value of the aqueous solution of a tazobactam salt is not limited insofar as it is 3 or lower. In view of crystallization efficiency, purity of the desired anhydrous crystals, and the like, the pH of the aqueous solution is usually adjusted to about 0.5 to about 1.5, and preferably about 0.6 to about 1.

To adjust the pH of the aqueous solution, acids are usually employed. Any acids can be used as long as they can adjust the aqueous solution to the pH values described above. Examples of such acids include nitric acid, hydrochloric acid, sulfuric acid, and like inorganic acids; and trifluoroacetic acid and similar organic acids. Among these acids, inorganic acids are preferable and hydrochloric acid is especially preferable. These acids can be used alone or in a combination of two or more species.

The pH adjustment with heating causes anhydrous tazobactam crystals to precipitate from the aqueous solution. The obtained anhydrous crystals of tazobactam can be readily isolated from the reaction system and purified according to conventional separation methods such as filtration, centrifugal separation, etc.

EFFECTS OF THE INVENTION

The anhydrous crystals of tazobactam of the present invention are excellent in storage stability, and therefore undergo substantially no decomposition even when stored for a long period of time at ambient temperature.

The anhydrous crystals of tazobactam of the present invention have pharmacological activity equivalent to that of known tazobactams. Specifically, the instant tazobactam in the form of anhydrous crystals irreversibly binds to various β-lactamases produced by microorganisms and exhibits properties of inhibiting β-lactamase activities. Therefore, the tazobactam is used in combination with various existing antibacterial agents that are inactivated by β-lactamases, allowing such various antibacterial agents to exhibit their inherent antibacterial activity against β-lactamase-producing microorganisms.

BEST MODE FOR CARRYING OUT THE INVENTION

An Example, Reference Example and Test Example are given below to describe the invention in more detail.

Reference Example 1

According to Example 1 of Japanese Patent No. 2648750, crystals of 2-methyl-2-triazolylmethylpenam-3-carboxylic acid S,S-dioxide (tazobactam) were prepared.

Specifically, 10 g of diphenylmethyl 2-methyl-2-triazolylmethylpenam-3-carboxylate S,S-dioxide was added to 80 ml of m-cresol that had been heated to a temperature of 50 to 55° C. These compounds were then reacted for two hours while maintaining this temperature.

After the reaction, 240 ml of methyl isobutyl ketone was added and the whole mixture was cooled to 0 to 5° C. Then, 23 ml of water and 2.3 g of sodium hydrogen carbonate were added, and extraction was performed. The organic layer, after being separated, was subjected to extraction again by adding 12 ml of water and 0.7 g of sodium hydrogen carbonate. The separated aqueous layers were combined, and washed with 18 ml of methyl isobutyl ketone and cooled to 0 to 5° C., and the pH was adjusted to 1 with 6N-hydrochloric acid. The precipitated 2-methyl-2-triazolylmethylpenam-3-carboxylic acid S,S-dioxide was separated by filtration, washed with a small amount of cold water and dried, giving white crystals of tazobactam.

The white crystals of tazobactam were subjected to differential scanning calorimetry. Differential scanning calorimetry was conducted using a THERMOFLEX (trade name) produced by Rigaku International Corporation, and the temperature was increased from 30 to 230° C. over 20 minutes. As a result, heat absorption specific to tazobactum hydrate was observed at 100 to 130° C. This observation confirmed that the white crystals of tazobactam obtained above contained water of crystallization.

The X-ray diffraction spectrum of the white crystals of tazobactam obtained above is as shown below. This X-ray diffraction spectrum was obtained with copper radiation through a monochromator, λ=1.5418 Å.

| d (interplanar spacings) | Relative intensities ($I/I_0$) |
|---|---|
| 9.2437 | 0.42 |
| 8.8734 | 0.18 |
| 8.6651 | 0.05 |
| 7.5317 | 0.19 |
| 7.2017 | 0.72 |
| 6.6516 | 0.30 |
| 6.1205 | 1.00 |
| 6.0130 | 0.44 |
| 5.9014 | 0.28 |
| 5.5902 | 0.38 |
| 5.4735 | 0.81 |
| 5.3681 | 0.36 |
| 5.1040 | 0.55 |
| 5.0350 | 0.19 |
| 4.8863 | 0.48 |
| 4.7513 | 0.11 |
| 4.5952 | 0.61 |
| 4.3246 | 0.23 |
| 4.1796 | 0.57 |
| 4.1373 | 0.23 |
| 3.8438 | 0.28 |
| 3.8081 | 0.42 |
| 3.7355 | 0.17 |
| 3.6897 | 0.14 |
| 3.6274 | 0.23 |
| 3.5957 | 0.23 |
| 3.5037 | 0.15 |
| 3.4741 | 0.17 |
| 3.3385 | 0.17 |
| 3.2853 | 0.10 |
| 2.9665 | 0.25 |
| 2.9099 | 0.23 |
| 2.8873 | 0.18 |
| 2.7250 | 0.25 |

Example 1

White crystals of tazobactam (15.9 g) as obtained in Reference Example 1 were added to 45 ml of water, and the pH was maintained at 5.5 to 6.0 using sodium hydrogen carbonate. The white crystals were dissolved to prepare an aqueous solution.

This aqueous solution was passed through a column packed with 21 ml of an ion-exchange resin (trade name: HP-20, manufactured by Mitsubishi Chemical Corporation). Subsequently, 75 ml of water was passed through the column, and the entire fractions thus obtained were combined.

An aqueous solution obtained by combining all the fractions was heated so as to adjust the temperature of the aqueous solution to 31.5° C. While maintaining said temperature, 6N-hydrochloric acid was added to so as to maintain the pH of 0.5 to 1.0. Precipitated crystals were filtered and dried, yielding 14.2 g of anhydrous white tazobactam crystals.

These white crystals were subjected to differential scanning calorimetry in the same manner as in Reference Example 1. As a result, heat absorption specific to hydrate was not observed at 100 to 130° C., demonstrating that these white crystals did not have water of crystallization.

Furthermore, elemental analysis of the white crystals revealed the results shown below, and the results confirmed that the white crystals were anhydrous tazobactam crystals.

Elemental Analysis (as $C_{10}H_{12}N_4O_5S$)

Calculated (%) H, 4.03; C, 40.00; N, 18.66.

Measured (%) H, 3.89; C, 39.90; N, 18.67.

The X-ray diffraction spectrum of the anhydrous white tazobactam crystals (obtained with copper radiation through a monochromator, λ=1.5418 Å) is as shown below:

| d (interplanar spacings) | Relative intensities ($I/I_0$) |
|---|---|
| 8.8556 | 0.21 |
| 8.6821 | 0.12 |
| 7.5445 | 0.36 |
| 6.6616 | 0.67 |
| 6.0293 | 0.89 |
| 5.9092 | 0.68 |
| 5.5902 | 0.54 |
| 5.1275 | 0.43 |
| 4.9078 | 1.00 |
| 4.7563 | 0.21 |
| 4.6525 | 0.18 |
| 4.3414 | 0.17 |
| 4.1796 | 0.70 |
| 3.5064 | 0.30 |
| 3.4795 | 0.23 |
| 3.2829 | 0.16 |
| 2.8878 | 0.44 |
| 2.7298 | 0.32 |

When the X-ray diffraction spectra of the tazobactam crystals obtained in Reference Example 1 are compared with the X-ray diffraction spectra of the tazobactam crystals obtained in Example 1, the former has twice as many spectrum peaks. Since it is clear that there are many peaks observed at different interplanar spacings, it was confirmed that the tazobactam crystals of Reference Example 1 and Example 1 are distinctly different.

Test Example 1

Ten grams each of tazobactam crystals obtained in Reference Example 1 and Example 1 were placed in test tubes. These test tubes were sealed and stored for 1 year at room temperature. Over the one-year period, the temperature fluctuated between 10 to 34° C.

Subsequently, purity each of the tazobactam crystals of Reference Example 1 and Example 1 was measured. Purity of the crystals of Example 1 was 100% and purity of the crystals of Reference Example 1 was 95%.

These facts clearly demonstrate that the anhydrous tazobactam crystals of the present invention are superior to known tazobactam crystals in storage stability.

The invention claimed is:
1. A method for producing anhydrous crystals of a β-lactam compound represented by formula (1):

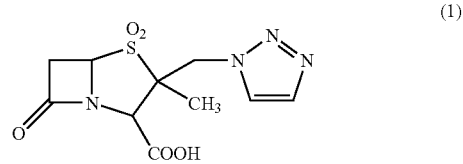

the method comprising:
heating an aqueous solution of a salt of the β-lactam compound represented by formula (1);
precipitating anhydrous crystals of the β-lactam compound by adjusting the pH of the aqueous solution to 3 or lower; and
isolating the precipitated β-lactam compound.

* * * * *